United States Patent [19]

Magnusson

[11] 4,007,735
[45] Feb. 15, 1977

[54] CERVICAL DILATION VIBRATOR
[75] Inventor: Bengt Uno Gunnar Magnusson, Enkoping, Sweden
[73] Assignee: Svedia Dental-Industri AB, Sweden
[22] Filed: Aug. 29, 1975
[21] Appl. No.: 609,086
[30] Foreign Application Priority Data
Aug. 29, 1974 Sweden .............................. 7410967
[52] U.S. Cl. ................................ 128/37; 128/341
[51] Int. Cl.² ........................................ A61H 1/00
[58] Field of Search ..................... 128/32, 34–37, 128/24.2, 47, 341
[56] References Cited
UNITED STATES PATENTS
719,675  2/1903  King .................................. 128/37
2,833,277  5/1958  Kline ................................. 128/35
3,363,623  1/1968  Atwell ............................... 128/36
3,375,381  3/1968  Tavel ................................. 128/36

Primary Examiner—Lawrence W. Trapp
Attorney, Agent, or Firm—Hill, Gross, Simpson, Van Santen, Steadman, Chiara & Simpson

[57] ABSTRACT

A vibrator having a detachable probe for dilating the cervix includes an eccentric at one end of the holder near the probe, a variable speed pneumatic motor at the other end of the holder, the center of gravity being nearer to the motor-end of the holder, and an adjustable source of pressure medium.

6 Claims, 5 Drawing Figures

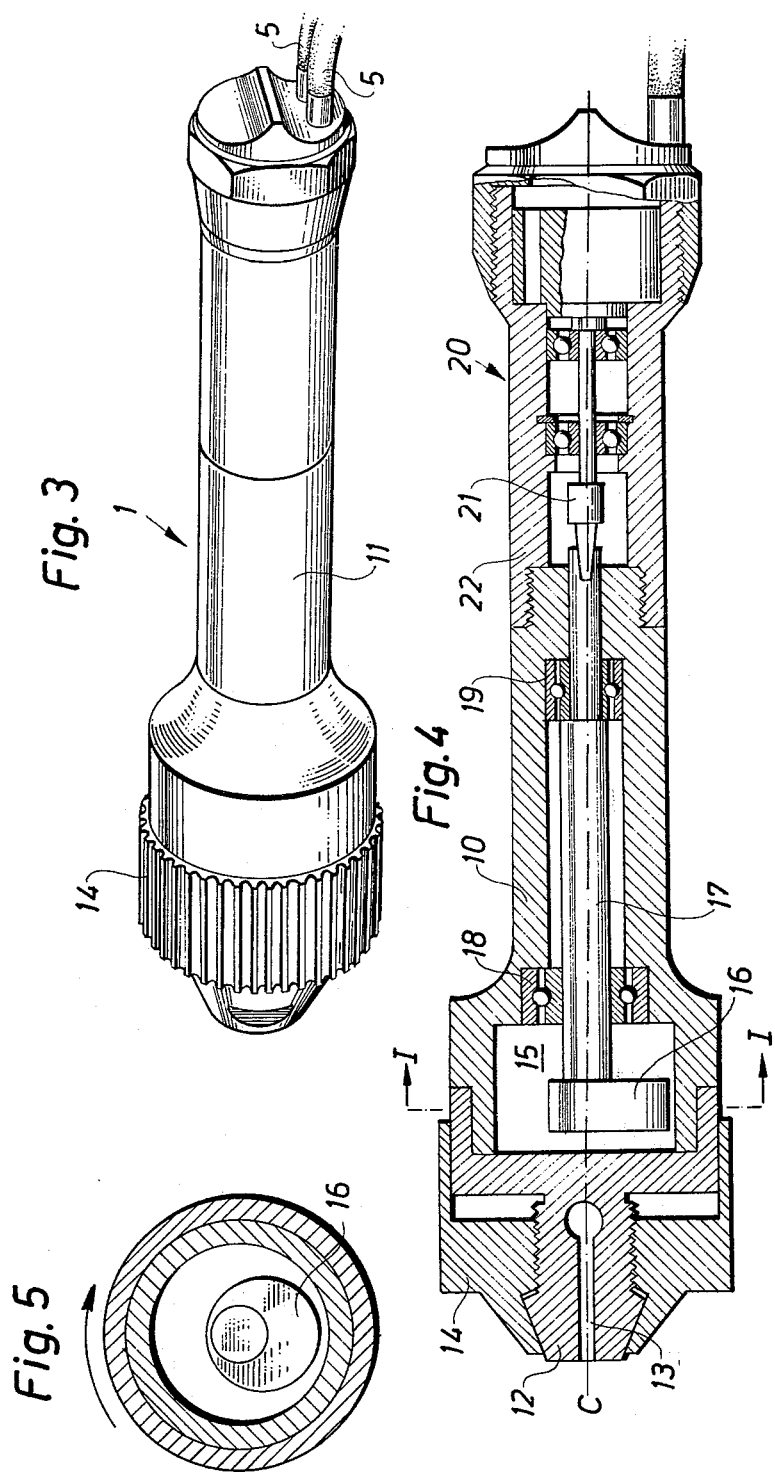

CERVICAL DILATION VIBRATOR

BACKGROUND OF THE INVENTION

1. Field of the Invention

The present invention relates in general to apparatus for vibrating body tissues, and especially to apparatus for vibrating cervical musculature.

2. Prior Art

It is known to treat body tissues and musculature by vibration in order to obtain relaxation of the musculature, e.g. to eliminate cramps or generally to make the body organs in question more soft and supple. A particular and very important application of such vibration of the parts of the body is in the form of the effect on the cervix during childbirth or legal abortion. This effect has the more immediate object of accelerating expansion of the cervical opening for thereby facilitating and speeding up parturition.

The treatment can be carried out in such a way that a spoon-like instrument, a so-called spatula, is manually placed against the cervical musculature and for a suited period of time is moved along its surface at the edge portion of the cervix. A periodic relaxation of the cervical smooth muscle is obtained by the vibratory effect.

A known apparatus for the purpose given above comprises a holder with a spatula firmly connected thereto. The holder is put in a state of transversal vibration by the rotation of a rotating body with an eccentric center of gravity about the longitudinal axis of the holder, whereby a dynamic imbalance generating the vibration is obtained. The body is rotated with the help of a rotatable flexible shaft coupled to the holder, the shaft being driven by a separate electric motor over a transmission capable of being coupled for different speeds. The said apparatus has given interesting results with relation to the desired effect on the cervix, but is burdened with certain drawbacks. These drawbacks are primarily bound up with the fact that the vibratory instrument itself is coupled to its driving apparatus by a mechanical transmission in the form of a flexible shaft, which causes the very sensitive manual guidance of the vibratory instrument to be made more difficult due to the stiffness of the transmission shaft. This stiffness also affects the sought-after vibratory character of the instrument.

SUMMARY OF THE INVENTION

The instrument should namely be so disposed that the desired vibration amplitude is preferably obtained at the end of the spatula applied to the cervical musculature, while the handle portion of the instrument where it is embraced by the operator's hand has as small a vibration amplitude as possible. The instrument should further also have greater flexibility with regard to vibration frequency than has been the case so far, and should also be easily sterilizable in an autoclave or with the help of hot air at a sufficiently high temperature, which has not been possible with apparatus in the prior art either.

Starting off from said prerequisite, the invention relates to a vibrator especially for dilatation of the cervical musculature, said vibrator comprising a manually carried and guided, substantially bar-shaped holder with a vibrating probe or spatula, applicable for treating the intended musculature, rigidly attachable to one end thereof and substantially extending in the longitudinal direction of the holder. For providing the desired vibration there is an eccentric vibrating body in the holder, rotatable about the longitudinal axis of the holder.

The vibrator according to the invention is characterized in that the eccentric body is situated between the holder handle and the connecting location for the vibratory instrument in the immediate vicinity of said connecting location, while the vibrating body is rotated by means of a motor arranged in the opposite end of the holder.

This motor suitably is a pneumatically driven rotating piston motor, and can preferably be infinitely variably adjustable for rotation between 1,000 and 10,000 revolutions per minute.

The pressure medium for driving the rotating piston motor is preferably provided from a separate fixed regulating means via a flexible hose connected to the vibrator. To achieve as far as possible the sought-after amplitude distribution over the vibrator, it is made with a distribution of mass such that its center of gravity is relatively close to the end of the holder where the motor is placed.

A vibrator made in the way set forth above, can be given an enclosed construction without difficulty, allowing sterilization of the incorporated elements in an autoclave or by hot air treatment at required temperatures.

The invention is described below in the shape of an embodiment while referring to the accompanying drawings.

ON THE DRAWINGS

FIG. 3 is a perspective view of the vibrator to a larger scale and with hoses connected; and FIG. 4 is an axial section through the vibrator;

FIG. 5 is a section along the line I—I in FIG. 4.

AS SHOWN ON THE DRAWINGS

Figure 1:
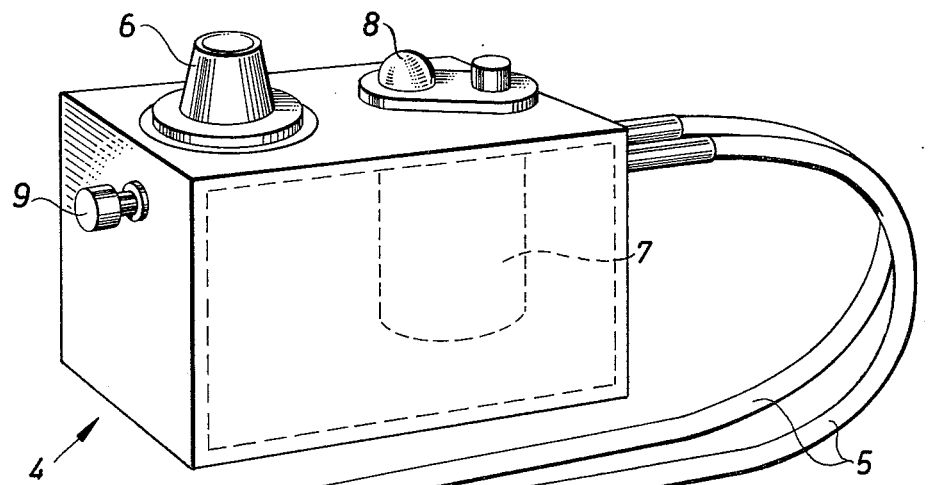
FIG. 1 shows schematically and in perspective a vibrator according to the invention with associated regulating means connected by hoses.
Figure 2:
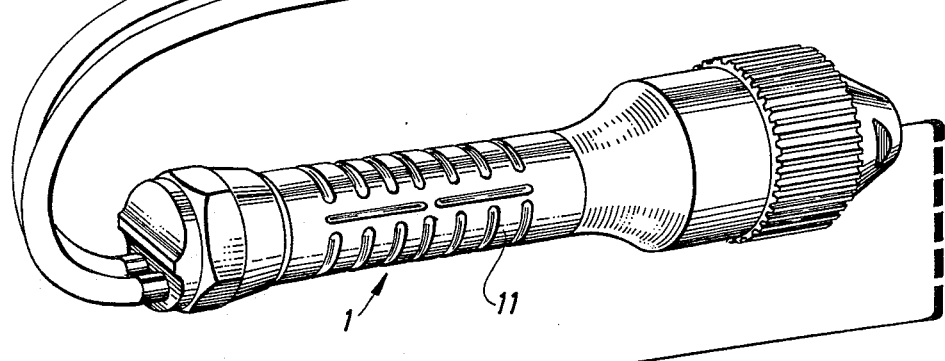
FIG. 2 shows a spatula and a probe, respectively, for connecting to the vibrator.
Figure 2:
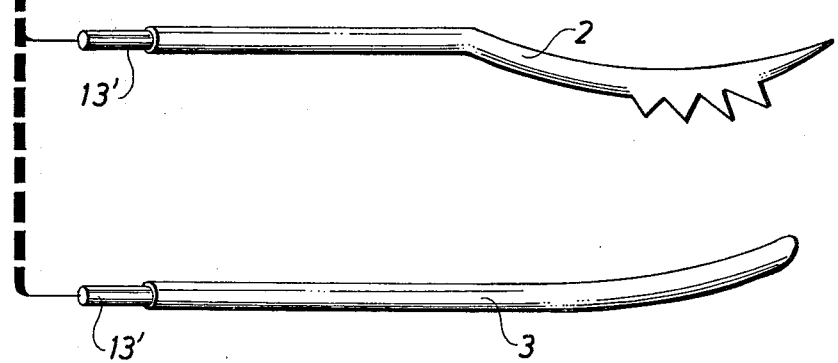

The vibrator 1 in FIG. 1 is coupled by means of hoses 5, 5 to the regulating means 4. The regulating means is of a conventional design and has the task of regulating the pressure medium required for driving the vibrator motor. The pressure medium normally consists of air, but any other gaseous medium not reacting with the surroundings can be used. The pressure medium is supplied through the inlet 9 and is thereafter passed to the regulating valve 6. With the aid of the regulating valve a suitable working pressure is set for the vibrator motor, e.g., 0.5 $kp/cm^2$. The pressure medium is filtered through a filter 7 and is provided with lubricant by means of the mist lubricator 8. Pressure medium is supplied via one of the hoses 5 to the vibrator motor and returns from it by means of another hose 5. Since the working pressure used is comparatively low and the required developed power is similarly limited, very light and flexible hoses can be used.

As may be more closely appreciated from FIGS. 3, 4 and 5, the vibrator 1 comprises a substantially cylindrical holder with a housing 10 arranged to be embraced by the operator's hand around the portion 11 shaped as a grip. In the forward end of the housing 10 a clamping chuck 12 operated by a clamping nut 14 is rigidly attached. The chuck 12 has gripping surfaces 13 arranged to accommodate the portion 13' of a spatula 2 or a probe 3, respectively, and rigidly to clamp it in the vibrator. At its free end the spatula 2 is shaped as a spoonlike instrument for application to the cervical musculature intended to be treated. The probe 3 is correspondingly shaped for applying to said musculature in the procedure of abortion.

The forward portion of the housing 10 at the clamping chuck is shaped with an interior expanded portion or cavity 15 for accommodating a vibrating body 16. This can for example be made in the form of a circular disc eccentrically mounted on a shaft 17 for rotation about the center line C—C of the vibrator. The shaft is carried in roller bearings 18, 19 and at its end opposite to the body 16 is connected through a coupling 21 to a rotating piston motor 20 for rotation by the motor. The rotating piston motor 20 can suitably be of the type described in the Swedish patent specification No. 323,839. The motor housing 22 forms a coaxial extension of the housing 10 along the center line C—C.

When in use, the vibrator described above, with the treatment instrument connected thereto, is gripped by the operator and moved with a suitably adjusted light pressure along the musculature to be treated. Transfer of vibrations from the instrument causes the intended relaxation of the cervical smooth muscle. The instrument preferably works with amplitudes of a fraction of a millimeter at the tip of the spatula or probe, respectively. Vibration frequency is preferably in the range 25–150 Hz but can be varied outside these limits as desired. By using a rotating piston motor of the kind stated, frequencies in the range 1–1,000 Hz can be obtained, corresponding to motor revolutions of up to 36,000 rpm.

Vibration of the instrument is achieved in a way known per se in principle, by dynamic imbalance occurring during rotation of the vibratory body 16. As has been discussed above, it is desirable that a comparatively large amplitude is obtained in the working portion of the treatment instrument, while comparatively small amplitude occurs in the portion of the vibrator where it is held in the operator's hand. The vibrator according to the invention is given a mass distribution such as is conducive to a vibrational state of the desired character. The mass of the vibrator is to a large extent collected in its rear portion in the shape of the relatively massive and heavy motor. From this the housing extends in a relatively light construction, with associated clamping chuck and treatment instrument connected thereto. The vibratory body 16 is located close to the attachment location of the treatment instrument, and at as great a distance from the main mass of the vibrator as is possible. Through this arrangement, the dynamic imbalance caused by the body 16 will have the greatest effect on the vibrator in its forward portion attached to the treatment instrument. On the other hand, the vibratory effect will be relatively limited near the driving motor of the vibrator. This condition in combination with the very flexible and mobile coupling of the vibrator driving motor by means of light and flexible hoses enables very sensitive and adaptable handling of the vibrator.

As in all medicinal apparatus, the requirement that the apparatus shall permit sterilization is also made for a vibrator of the kind in question. Such sterilization can for example take place by treatment in an autoclave or by hot air sterilization. In the former case a process or water vapor temperature of up to 158° C must be reckoned with, and in the latter case a somewhat higher air temperature, i.e. up to 185° C. The vibrator according to the invention is an implement which allows sterilization at the stated temperatures. For the process, it is only necessary to remove the hoses for pressure medium to the motor, and to plug the corresponding inlet and outlet. The vibrator has a completely enclosed construction in which the incorporated parts are made of material which can be exposed to said temperatures without damage. The vibrator housing, clamping chuck and motor housing can for example be made of a corrosion resistant steel alloy having a conventional composition suited for medicinal use.

Although various minor modifications might be suggested by those versed in the art, it should be understood that I wish to embody within the scope of the patent warranted hereon, all such embodiments as reasonably and properly come within the scope of my contribution to the art.

I claim as my invention:

1. A vibrator for internal use on a human body, especially for dilation of cervical musculature, comprising:
   a. a substantially bar-shaped holder having a handle portion for manual holding and guiding of the vibrator;
   b. a vibratable solid probe of elongated configuration to extend into the body to be applicable to said musculature and extending in the longitudinal direction of said holder;
   c. coupling means rigidly detachably interconnecting one end of said holder and said solid probe;
   d. an eccentric vibrator body rotatable about the longitudinal axis of and situated within said holder axially between said handle portion and said coupling means in the immediate vicinity of said coupling means;
   e. a motor disposed in the opposite end of said holder and rotatingly coupled to said eccentric body; and
   f. the vibrator having a center of gravity lying closer to the motor end of said holder than to said one end of said holder;
whereby the rigid system formed by said holder and said probe is given an oscillatory movement about the longitudinal axis of said holder with its minimum oscillating peak situated in the region of said handle portion.

2. A vibrator as claimed in claim 1 in which said motor is a pneumatically driven rotating piston motor.

3. A vibrator as claimed in claim 2, including:
   a. a separate fixed fluid pressure regulating means of the manually setable type adapted to provide pressure medium at selected pressure and volume; and
   b. a flexible hose interconnecting said regulating means and said piston motor;
whereby the speed of said motor is regulated.

4. A vibrator as claimed in claim 1 in which said motor is infinitely variably regulatable for rotation between 1,000 and 10,000 revolutions per minute.

5. A vibrator as claimed in claim 1 in which said probe, said holder and the components in said holder consist of materials which are resistant to sterilization air having a temperature up to 185° C, and are resistant to sterilization water vapor having a temperature up to 158° C.

6. A vibrator as claimed in claim 1, said holder being of closed construction and sealing said vibrator body and said motor from a sterilization ambient.

* * * * *